United States Patent [19]

Sircar et al.

[11] Patent Number: 4,508,718

[45] Date of Patent: Apr. 2, 1985

[54] CARDIOTONIC AND ANTIHYPERTENSIVE OXADIAZINONE COMPOUNDS

[75] Inventors: Ila Sircar, Ann Arbor; Michael H. Cain, Saline; John G. Topliss, Ann Arbor, all of Mich.

[73] Assignee: Warner-Lambert Company, Morris Plains, N.J.

[21] Appl. No.: 571,057

[22] Filed: Jan. 16, 1984

[51] Int. Cl.$^3$ .................. A61K 31/535; C07D 413/10
[52] U.S. Cl. ........................................ 514/238; 544/68
[58] Field of Search ...................... 544/68; 424/248.51

[56] References Cited

FOREIGN PATENT DOCUMENTS 85227 8/1983 European Pat. Off. .
86301 8/1983 European Pat. Off. .

Primary Examiner—Richard L. Raymond
Attorney, Agent, or Firm—Ronald A. Daignault

[57] ABSTRACT

Cardiotonic and antihypertensive imidazole or triazole substituted phenyl-4H-1,3,4-oxadiazin-5(6H)-ones are described including pharmaceutical compositions and methods of administering the active ingredients. The subject compounds may be manufactured by ring closing appropriate derivatives of benzoic acid-2-(haloacetyl)hydrazides with sodium hydride.

12 Claims, No Drawings

CARDIOTONIC AND ANTIHYPERTENSIVE OXADIAZINONE COMPOUNDS

BACKGROUND OF THE INVENTION

Certain heterocyclic, phenyl, and substituted phenyl-oxadiazin-ones, -thiadiazin-ones and -triazin-ones have been described in Australian patent application Nos. 8290-158 and 8290-006.

The present invention relates to novel imidazole or triazole substituted phenyl-4H-1,3,4-oxadiazin-5(6H)-one compounds useful as cardiotonic and/or antihypertensive agents.

SUMMARY OF THE INVENTION

The present invention relates to a compound of the formula

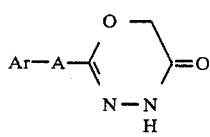

wherein Ar is a group of the formula

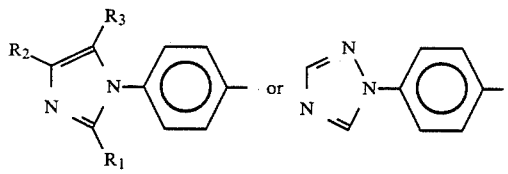

in which $R_1$, $R_2$, and $R_3$ are each independently hydrogen, lower alkyl or $CH_2OH$, and $R_2$ and $R_3$ when taken together may form a saturated or unsaturated five or six membered ring; A is a bond, 1-carbon alkylene or 2-4 carbon alkenylene, and pharmaceutically acceptable acid addition salts thereof.

Another aspect of the present invention relates to a cardiotonic composition for increasing cardiac contractility and/or an antihypertensive composition for lowering blood pressure, said composition comprising an effective amount of a compound of formula I and a pharmaceutically acceptable carrier.

The present invention further relates to the method for increasing cardiac contractility and/or lowering blood pressure in a mammal requiring such treatment which comprises administering orally or parenterally in a solid or liquid dosage form to such mammal an effective amount of a compound of the formula I and a pharmaceutically acceptable salt thereof together with a pharmaceutical carrier.

DETAILED DESCRIPTION

The compounds of formula (I) are useful both in the free base form and in the form of acid addition salts. Both forms are within the scope of the invention. The acid addition salts are a more convenient form for use; and in practice, use of the salt form amounts to use of the base form. In practicing the invention, it was found convenient to form the sulfate, phosphate, or methanesulfonate salts. However, other appropriate pharmaceutically acceptable salts within the scope of the invention are those derived from mineral acids such as hydrochloric acid and sulfamic acid; and organic acids such as ethanesulfonic acid, benzenesulfonic acid, p-toluenesulfonic acid and the like, giving the hydrochloride, sulfamate, ethanesulfonate, benzenesulfonate, p-toluenesulfonate, and the like, respectively. The compounds of formula I can also form salts with acetic acid, propionic acid, oxalic acid, malonic acid, glycolic acid, maleic acid, and fumaric acid.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The term "lower" in reference to alkyl means a straight or branched hydrocarbon chain of one to six carbon atoms such as, for example, methyl, ethyl, propyl, isopropyl, and the like.

The term "1-carbon alkylene" means a straight or branched hydrocarbon chain such as, for example, methylene, ethylene, propylene, 1-methyl-ethylene, 1-methyl-propylene, and the like.

The term "2-4 carbon alkenylene" means a straight or branched hydrocarbon chain containing a double bond in the chain such as, for example, vinylene, ethenylene, propenylene, 1-methyl-ethenylene-, 1-methyl-propenylene, and the like.

Alternate embodiments of the present invention include a compound of formula I wherein A is a bond, or a compound of formula I wherein Ar is a group of the formula

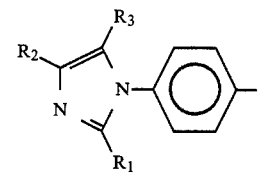

in which $R_1$, $R_2$, and $R_3$ are each independently hydrogen, methyl, or ethyl and $R_2$ and $R_3$ when in which $R_1$, $R_2$, and $R_3$ are each independently hydrogen, methyl, or ethyl and $R_2$ and $R_3$ when taken together may form a 6-membered saturated or unsaturated ring and pharmaceutically acceptable acid addition salts thereof.

Particular embodiments of the present invention include:

2[4-(1H-imidazolyl-1-yl)phenyl]-4H-1,3,4-oxadiazin-5(6H)-one;

2[4-(1H-benzimidazol-1-yl)phenyl]-4H-1,3,4-oxadiazin-5(6H)-one;

2-[4-(1H-2-methylimidazol-1-yl)phenyl]-4H-1,3,4-oxadiazin-5(6H)-one;

2-[4-(1H-4,5,6,7-tetrahydro-1H-benzimidazol-1-yl)phenyl]-4H-1,3,4-oxadiazin-5(6H)-one;

2-[4-(1H-4-methylimidazol-1yl)phenyl]-4H-1,3,4-oxadiazin-5(6H)-one;

2-[4-(1H-2-ethyl-4-methylimidazol-1-yl)phenyl]-4H-1,3,4-oxadiazin-5(6H)-one; and pharmaceutically acceptable acid addition salts thereof.

The compounds of the present invention may be prepared by the following general reaction scheme:

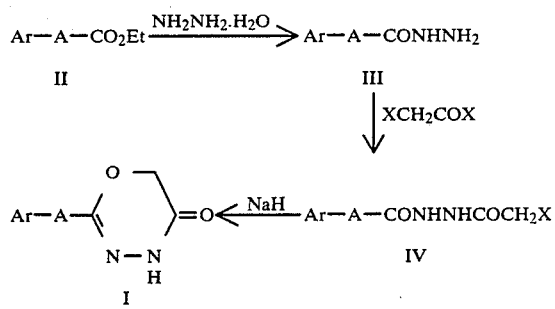

wherein Ar and A are as defined above and X is halogen, preferably bromine or chlorine.

The aromatic ester of formula II is treated with hydrazine hydrate at the reflux temperature of the solvent employed. Solvents are especially alcoholic solvents, such as ethanol, isopropanol, n-butanol and the like. The resulting hydrazine is treated with a haloacetyl halide in a nonreactive solvent, such as N,N'-dimethylformamide at or near ambient temperature. The resulting compound of formula IV is then ring closed with sodium hydride in a nonreactive solvent, such as N,N'-dimethylformamide, at elevated temperatures, such as between about 60° and 150° C. and preferably near 100° C.

Accordingly, the present invention includes a process for preparing a compound of formula I which comprises reacting a compound of the formula Ar—A—CONHNHCOCH$_2$X, wherein X is halogen and Ar and A are as defined above, with sodium hydride in a nonreactive solvent at elevated temperatures and, if desired, converting the resulting free base to a pharmaceutically acceptable acid addition salt thereof by known means.

The starting material of formula II, wherein A is a bond, may be prepared by reacting ethyl 4-fluorobenzoate with an imidazole or triazole in the presence of sodium hydride.

Compounds of formula II, wherein A is a 2–4 carbon alkenylene group may be prepared by reacting the appropriate imidazole or triazole with 4-fluorobenzaldehyde as described in Chem. Abstr. 65, 13686 (1966). The resulting heterocyclic phenyl carboxaldehyde is condensed with malonic acid to give the alkenylene compound which, if desired, may be reduced catalytically to a compound of formula II where A is a carbon alkylene chain.

The usefulness of the compounds of the present invention as cardiotonic agents is demonstrated by their effectiveness in standard pharmacological test procedures, for example, in causing a significant increase in the myocardial contractility in the pentobarbital-anesthetized dog with low or minimal changes in heart rate and blood pressure. This test procedure is described in the following paragraphs.

Test for In Vivo Myocardial Intropic Activity in Anesthetized Dog

This screen consists of determining the effects of increasing intravenous doses of compound on mycardial contractility (dP/dt max of left ventricular blood pressure), heart rate, and aortic blood pressure of the pentobarbital-anesthetized dog.

Methods

Adult mongrel dogs of either sex are anesthetized with pentobarbital, 35 mg/kg, IV, and are subsequently maintained under anesthesia with a continuous infusion of pentobarbital, 3.5 mg/kg/hour. The trachea is intubated but the animals are permitted to breathe spontaneously. A cannula is inserted into the femoral vein for administrating test agents. A Millar catheter tip pressure transducer or a fluid filled catheter is inserted into the ascending aorta via the femoral artery for measuring aortic blood pressure. A Millar catheter tip pressure transducer is passed into the left ventricle via the left carotid artery for measuring left ventricular blood pressure. Needle electrodes are placed subcutaneously for recording a lead II electrocardiogram (ECG).

Left ventricular and aortic blood pressures are recorded on a strip chart recorder. Heart rate, using a biotachometer triggered from the R wave of the ECG, and the first derivative of left ventricular blood pressure (dP/dt), obtained with a differentiator amplifier coupled to the corresponding pressure amplifier, are also recorded. A period of at least 30 minutes is utilized to obtain control data prior to administration of test compound.

Depending on solubility, the compounds are dissolved in 0.9% saline solution or in dilute HCl or NaOH (0.1 or 1.0 N) and are diluted to volume with normal saline. Ethanol or dimethylacetamide can be used as solvents if adequate dilutions can be made. Appropriate vehicle controls are administered when needed.

Each dose of the test compound is administered in a volume of 0.1 ml/kg over a period of one minute.

When tested by the above-described Anesthetized Dog Procedure, the compounds of the present invention, for example, compound Ia of Example 1, when administered intravenously at about 0.01 to 0.31 mg/kg cause dose related significant increases in cardiac contractility with only low or minimal changes in heart rate and a moderate reduction in blood pressure. Accordingly, the compounds of the present invention are also useful as antihypertensive agents.

The results are summarized in the following table:

TABLE

Test Result of 2-[4-(1H—imidazol-1-yl)phenyl]-4H—1,3,4-oxadiazin-5(6H)—one (Ia), using Anesthetized Dog Procedure.

| Compound | Dose mg/kg | Myocardial Contractility | Heart Rate | Blood Pressure |
|---|---|---|---|---|
| Ia | .01 | 13 | 1 | 1 |
|  | .03 | 42 | 0 | 0 |
|  | 0.1 | 87 | 6 | −2 |
|  | 0.3 | 165 | 17 | −5 |
|  | 1.0 | 193 | 11 | −15 |

(Percent Change)

The following example will further illustrate the invention without limiting it thereto.

EXAMPLE 1

2-[4-(1H-imidazol-1yl)phenyl]-4H-1,3,4-oxadiazin-5(6H)-one (Ia)

A solution of 5 g (17.9 m mol) of 4-(1H-imidazol-1-yl)-benzoic acid-2-(choroacetyl)hydrazide monohydrochloride (IVa) in 70 ml of N,N-dimethylformamide containing 790 mg of 60% sodium hydride is heated to 100° C. for 1 h. The solvent was evaporated under reduced pressure. The residue was dissolved in a mixture of chloroform and isopropanol and filtered over silica gel. The filtrate was evaporated and the residue was triturated with methanol and filtered to give 1 g of Ia, mp 252°–254° C. Anal. Calcd. for $C_{12}H_{10}N_4O_2$; C, 59.50; H, 4.16; N, 23.13; Found C, 59.40; H, 4.20; N, 22.97.

By following the procedure of Example 1 the following additional compounds were prepared.

Ib. 2-[4-(1H-benzimidazol-1-yl)phenyl]-4H-1,3,4-oxadiazin-5(6H)-one, mp 225°–227° C.

Ic. 2-[4-(1H-2-methyl-imidazol-1-yl)phenyl]-4H-1,3,4-oxadiazin-5(6H)-one, monohydrochloride, mp 287°–289° C.

Id. 2-[4-(1H-4,5,6,7-tetrahydro-1H-benzimidazol-1-yl)phenyl]-4H-1,3,4-oxadiazin-5(6H)-one, mp 242°–244° C.

Ie. 2-[4-(1H-4-methyl-imidazol-1-yl)phenyl]-4H-1,3,4-oxadiazin-5(6H-one, mp 228°—234° C.

PREPARATIVE EXAMPLES

Ethyl 4-1H-imidazol-1-yl)benzoate (IIa):

A solution of 34 g (0.5 mol) of imidazole in 180 ml of DMSO is added slowly to an ice-cold suspension of 24 g of 50% sodium hydride in 100 ml of toluene. Temperature of the reaction mixture is maintained around 10° C. After the addition is over, the reaction mixture is stirred at room temperature for of two to three hours. Ethyl 4-fluorobenzoate (84.12, 0.5 mol) is then added followed by heating the mixture at 100°–110° C. for 12 hours. The reaction mixture is cooled, poured into excess water and filtered. The solid is crystallized from isopropanol to give 80.6 g of IIa, mp 98.5°–99.5° C.

Anal Calcd. for $C_{12}H_{12}N_2O_2$; C, 66.65%; H, 5.59%; N, 12.96%. Found: C, 66.63%, H, 5.39%; N, 12.89%.

4-[1 H-imidazol-1-yl]benzhydrazide (IIIa):

A mixture of 80.6 g of 1 and 25.6 g of 80% hydrazine hydrate in 400 ml of n BuOH was refluxed for 12 hours. The reaction mixture was cooled and filtered to give 68 g of IIIa, mp 222°–223° C.

4-(1 H-imidazol-1-yl)-benzoic acid-2-(chloroacteyl) hydrazide, monohydrochloride (IVa):

Chloroacetylchloride (2 ml, 25.1 m mol) is added to a solution of 1 g (4.95 m mol) of IIIa in 20 ml of N,N-dimethylformamide at room temperature with stirring for 4 h. Ether is added to precipitate the hydrochloride salt of the product. The white solid is filtered, washed with ether and air-dried to give 1.1 g of IVa, mp 221°–223° C.

We claim:

1. A compound of the formula

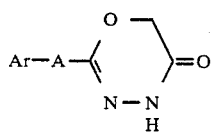

wherein Ar is a group of the formula

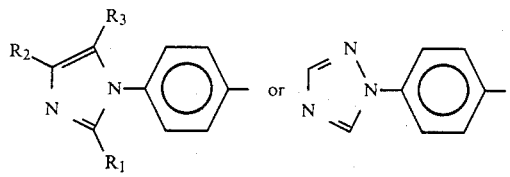

in which $R_1$, $R_2$, and $R_3$ are each independently hydrogen, lower alkyl or $CH_2OH$, and $R_2$ and $R_3$ when taken together may form a five- or six-membered saturated or unsaturated ring; A is a bond, 1-4 carbon alkylene or 2-4 carbon alkenylene, and pharmaceutically acceptable acid addition salts thereof.

2. A compound according to claim 1, wherein A is a bond.

3. A compound according to claim 2, wherein Ar is a group of the formula

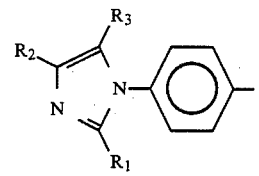

in which $R_1$, $R_2$, and $R_3$ are each independently hydrogen, methyl, or ethyl and $R_2$ and $R_3$ when taken together form a six-membered saturated or unsaturated ring.

4. A compound according to claim 3, and being 2-[4-( H-imidazol-1-yl)-phenyl]-4H-1,3,4-oxadiazin-5(6H)-one.

5. A compound according to claim 3, and being 2-[4-(1H-benzimidazol-1-yl)-phenyl]-4H-1,3,4-oxadiazin-5(6H)-one.

6. A compound according to claim 3, and being 2-[4-(1H-2-methylimidazol-1-yl)-phenyl]-4H-1,3,4-oxadiazin-5(6H)-one.

7. A compound according to claim 3, and being 2[-4-(1H-4,5,6,7-tetrahydro-1H-benzimidazol-1-yl)-phenyl]-4H-1,3,4-oxadiazin-5(6H)-one.

8. A compound according to claim 3, and being 2-[4-( H-methylimidazol-1-yl)-phenyl]-4H-1,3,4-oxadiazin-5(6H)-one.

9. A compound according to claim 3, and being 2-[4-(1 H-2-ethyl-4-methylimidazol-1-yl)-phenyl]-4H-1,3,4-oxadiazin-5(6H)-one.

10. A pharmaceutical composition comprising an effective amount of a compound according to claim 1 and a pharmaceutically acceptable carrier.

11. A method for increasing cardiac contractility in a mammal requiring such treatment which comprises administering to such mammal an effective amount of a compound according to claim 1 with a pharmaceutically acceptable carrier.

12. A method for lowering blood pressure in a mammal requiring such treatment which comprises administering to such mammal an effective amount of a compound according to claim 1 with a pharmaceutically acceptable carrier.

* * * * *